US 12,023,444 B2

(12) United States Patent
Eifler

(10) Patent No.: US 12,023,444 B2
(45) Date of Patent: Jul. 2, 2024

(54) CONNECTING SOCKET AND ROTARY SLEEVE FOR RESPIRATION

(71) Applicant: Loewenstein Medical Technology S.A., Luxembourg (LU)

(72) Inventor: Martin Eifler, Glueckstadt (DE)

(73) Assignee: LOEWENSTEIN MEDICAL TECHNOLOGY S.A., Luxembourg (LU)

(*) Notice: Subject to any disclaimer, the term of this patent is extended or adjusted under 35 U.S.C. 154(b) by 1770 days.

(21) Appl. No.: 15/621,024

(22) Filed: Jun. 13, 2017

(65) Prior Publication Data

US 2017/0361051 A1 Dec. 21, 2017

(30) Foreign Application Priority Data

Jun. 16, 2016 (DE) .......................... 102016007302.0

(51) Int. Cl.
*A61M 16/08* (2006.01)
*A61M 16/00* (2006.01)
*A61M 16/06* (2006.01)
*A61M 39/10* (2006.01)

(52) U.S. Cl.
CPC ........ *A61M 16/0816* (2013.01); *A61M 16/06* (2013.01); *A61M 16/0825* (2014.02); *A61M 16/0875* (2013.01); *A61M 39/10* (2013.01); *A61M 16/00* (2013.01)

(58) Field of Classification Search
CPC .......... A61M 16/0816; A61M 16/0825; A61M 16/06; A61M 16/0875; A61M 39/10; A61M 16/00; F16B 7/02; F16B 7/22; F16B 7/04; F16B 7/0406; F16B 7/0413; Y10T 403/7037; Y10T 403/7039
See application file for complete search history.

(56) References Cited

U.S. PATENT DOCUMENTS

| 3,731,684 | A | | 5/1973 | Spiegel | |
|---|---|---|---|---|---|
| 5,937,851 | A | * | 8/1999 | Serowski | A61M 16/06 128/202.27 |
| 6,402,207 | B1 | * | 6/2002 | Segal | A61M 39/10 285/330 |
| 2003/0116963 | A1 | * | 6/2003 | Teuscher | A61M 16/08 285/179 |
| 2003/0196656 | A1 | * | 10/2003 | Moore | A61M 16/06 128/201.22 |

(Continued)

FOREIGN PATENT DOCUMENTS

| CN | 204745354 U | 11/2015 |
|---|---|---|
| DE | 3339988 A1 | 5/1985 |

(Continued)

*Primary Examiner* — Kendra D Carter
*Assistant Examiner* — Paige Kathleen Bugg
(74) *Attorney, Agent, or Firm* — Abel Schillinger, LLP

(57) ABSTRACT

Disclosed is a respiratory device comprising a connecting socket which is inserted at least partially into a rotary sleeve and is latched thereto. The connecting socket and the rotary sleeve are disposed between a respiration hose and a patient interface, the connecting socket having an external diameter which is smaller than the internal diameter of the rotary sleeve. The rotary sleeve comprises on its inner side latching elements which engage in latching elements on the external diameter of the socket.

18 Claims, 6 Drawing Sheets

(56) References Cited

U.S. PATENT DOCUMENTS

| | | | | |
|---|---|---|---|---|
| 2004/0025881 A1* | 2/2004 | Gunaratnam | ......... | A61M 16/06 128/206.15 |
| 2005/0205096 A1* | 9/2005 | Matula | .............. | A61M 16/0666 128/207.11 |
| 2006/0076017 A1* | 4/2006 | Walker | .................. | A61M 16/06 128/205.24 |
| 2007/0215147 A1* | 9/2007 | Ho | ........................ | A61M 16/08 128/200.24 |
| 2007/0277828 A1* | 12/2007 | Ho | ........................ | A61M 16/08 128/206.21 |
| 2008/0276943 A1* | 11/2008 | Eifler | ...................... | F16L 27/04 128/206.21 |
| 2010/0083969 A1* | 4/2010 | Crumblin | .............. | A61M 16/06 128/206.21 |
| 2012/0055471 A1 | 3/2012 | Hadas et al. | | |
| 2015/0151071 A1 | 6/2015 | Von Moger et al. | | |

FOREIGN PATENT DOCUMENTS

| | | | |
|---|---|---|---|
| EP | 2465564 | A1 | 6/2012 |
| WO | 0078381 | A1 | 12/2000 |
| WO | 2006133480 | A1 | 12/2006 |

* cited by examiner

CONNECTING SOCKET AND ROTARY SLEEVE FOR RESPIRATION

CROSS-REFERENCE TO RELATED APPLICATIONS

The present application claims priority under 35 U.S.C. § 119 of German Patent Application No. 10 2016 007 302.0, filed Jun. 16, 2016, the entire disclosure of which is expressly incorporated by reference herein.

BACKGROUND OF THE INVENTION

1. Field of the Invention

The present invention relates to a respiratory device configured as a patient interface. Respiratory devices are of importance to patients who suffer from a disturbance of the respiratory air or oxygen supply, wherein, via a patient interface which can be configured as a full-face mask, nose mask or nasal pillow mask, respiratory gas, or oxygen-enriched air, can be fed with a positive pressure support to the patient.

2. Discussion of Background Information

In order to connect the patient interface to the respiration hose, a rotary sleeve, which is connected via a releasable snap joint to a connecting socket of the mask, is generally used. This enables hose forces to be diverted through the use of a rotary function and allows the patient to easily separate the connection during a break in therapy.

The connecting socket is designed, for instance, as an elbow having a ball joint. The snap joint between the connecting socket and the rotary sleeve is generally realized by snap hooks in the connecting socket. For this, the connecting socket is of slotted design, so that resilient elements are obtained. These have the drawback that they can easily break off. As a result of the slotting, a small overlap between connecting socket and rotary sleeve is obtained, so that increased leaks occur.

A further problem is posed by the removal/release of the hose from the rotary sleeve. The hose coupling is much more firmly connected to the rotary sleeve than is the rotary sleeve to the elbow. For the release of the very tightly fitting connection of the hose coupling of the respiration hose from the rotary sleeve, only a very small holding or operating surface is available, which specifically for elderly patients or patients with restricted motility, is very difficult to handle.

In view of the foregoing, it would be advantageous to have available a device of the type stated in the introduction such that high functionality, improved handling and high reliability is provided.

SUMMARY OF THE INVENTION

The present invention provides a respiratory device comprising or consisting of a connecting socket which is inserted at least partially into a rotary sleeve and is latched thereto. The connecting socket and the rotary sleeve are disposed between a respiration hose and a patient interface. Further, the connecting socket has an external diameter which is smaller than the internal diameter of the rotary sleeve, and the rotary sleeve has on its inner side latching elements, which engage in latching elements on the external diameter of the socket.

In one aspect, the socket may intrude with at least about 30%, e.g., at least about 60%, or at least 80% of its length L into the rotary sleeve.

In another aspect, the rotary sleeve may comprise on its inner wall a stop for the socket.

In yet another aspect, the respiration hose may comprise a hose coupling having an internal diameter $D6$ which is greater than the external diameter $D5$ of the rotary sleeve.

In a still further aspect, the rotary sleeve may be conical, so that the external diameter $D5$ of the rotary sleeve slowly widens up to the end facing the connecting socket.

In another aspect, the rotary sleeve may comprise a conical inner face.

In another aspect, the rotary sleeve may comprise symmetrical extensions (lugs) of the one-piece (unitary) outer wall.

In another aspect, the lugs may comprise on their inner wall an undercut or a latching portion, which serves for the latching connection to the socket.

In another aspect, the rotary sleeve may have an internal diameter $D4$ which is smaller than the external diameter $D3$ of the connecting socket.

In another aspect, the external diameter $D3$ of the connecting socket may widen conically into the external diameter $D2$.

In another aspect, the socket, for the latching to the rotary sleeve, may comprise a circumferential bevel or a step in the outer wall.

In another aspect, the socket may taper behind the step and may have the external diameter $D1$, which is smaller than $D2$ or $D3$.

In another aspect, the lugs may reach with the undercut over the step and thus may form a snap joint between rotary sleeve and socket.

In another aspect, an axial displacement between the rotary sleeve and the socket may be avoided by an end stop, against which the socket butts, in the rotary sleeve.

BRIEF DESCRIPTION OF THE DRAWINGS

The following drawings illustrate the structure of a hose attachment to a patient interface. In the drawings.

DETAILED DESCRIPTION OF EXEMPLARY EMBODIMENTS

Figure 1:
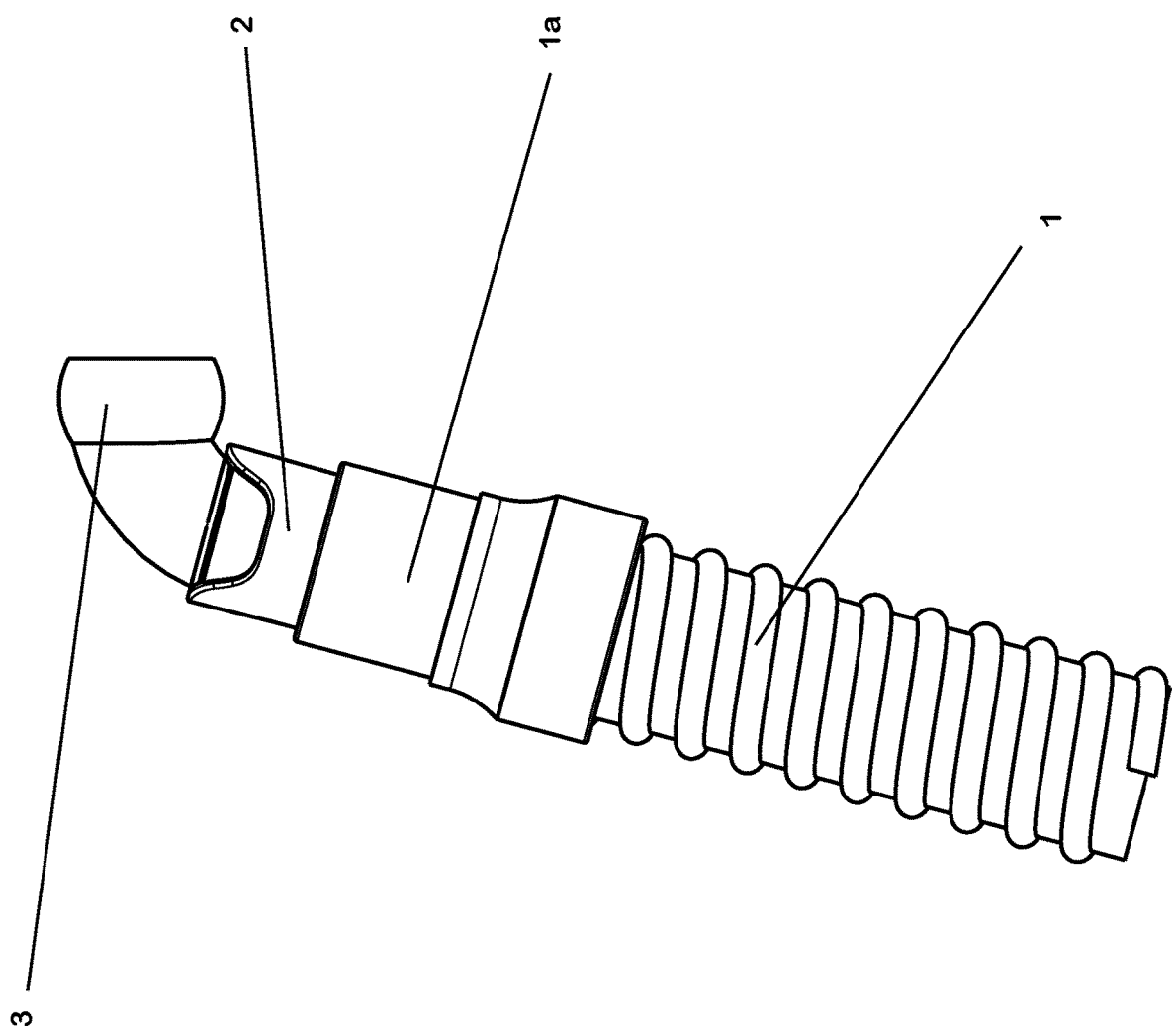
FIG. 1 shows a connecting socket with rotary sleeve and respiration hose.
Figure 2:
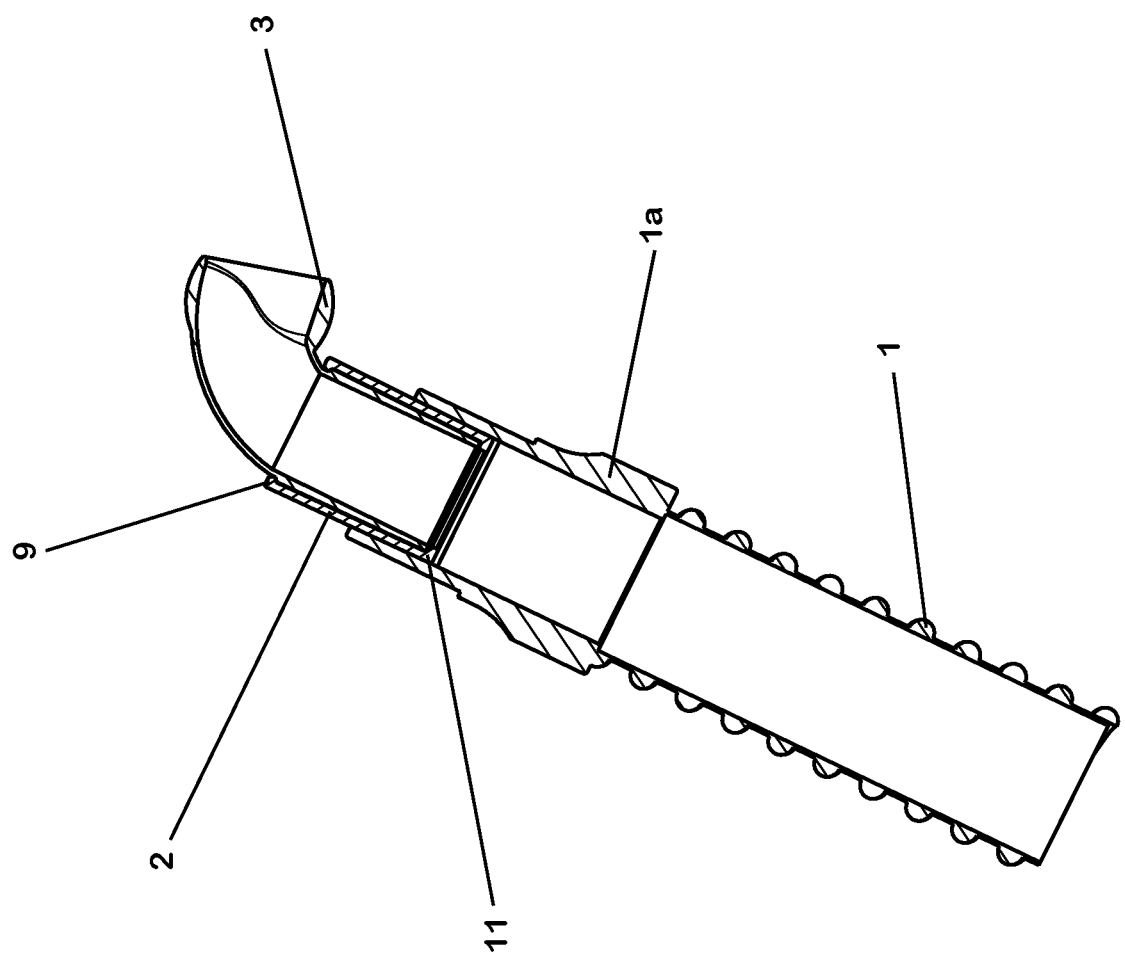
FIG. 2 is a sectional representation of the structure.
Figure 3:
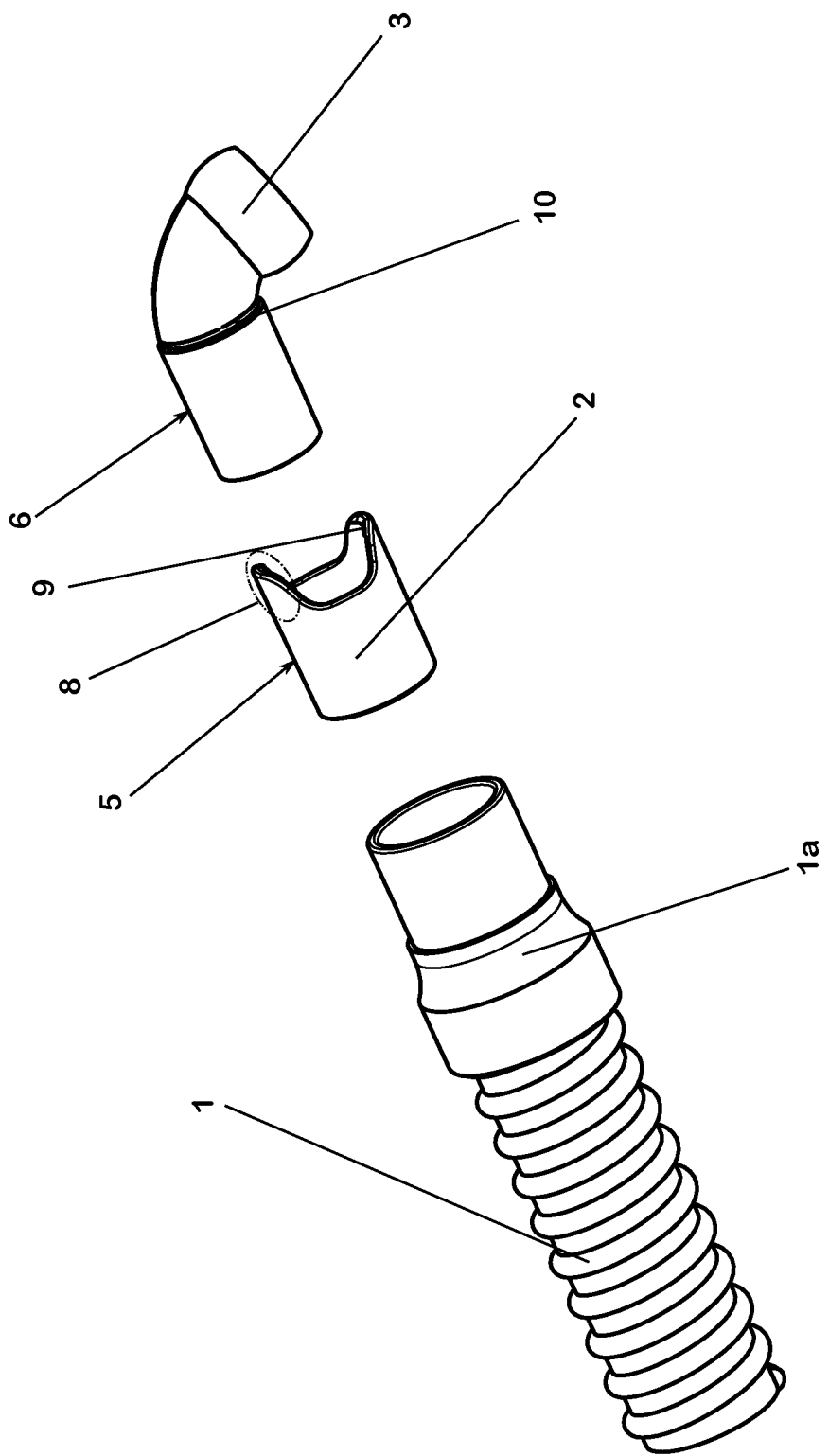
FIG. 3 is an exploded representation of the structure.
Figure 4:
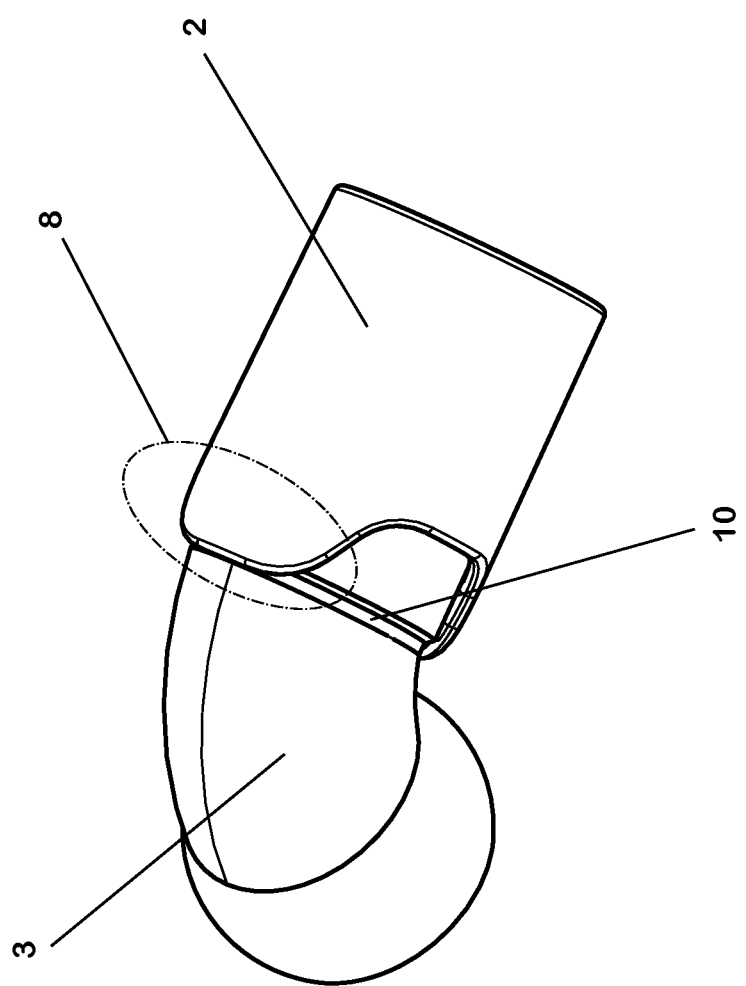
FIG. 4 shows the rotary sleeve connected to the connecting socket.
Figure 5:
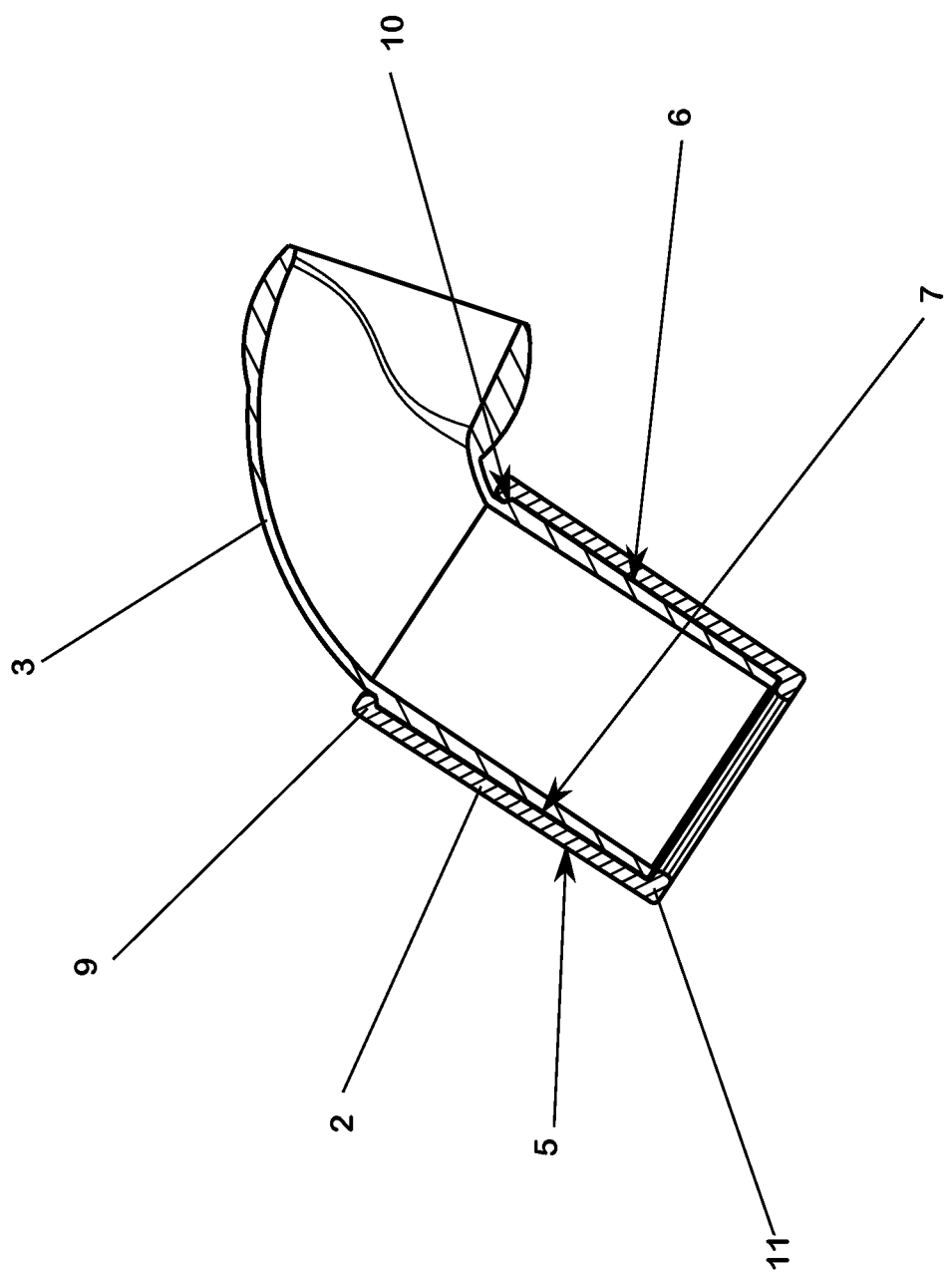
FIG. 5 is a sectional view through rotary sleeve and connecting socket.

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show details of the present invention in more detail than is necessary for the fundamental understanding of the present invention, the description in combination with the drawings making apparent to those of skill in the art how the several forms of the present invention may be embodied in practice.

For the respiration, the hose (1), at whose ends is found a hose coupling (I a), is connected on the patient side, via a rotary sleeve (2) and a connecting socket (6), to the patient interface (4) (not represented). The hose coupling (1a) of the respiration hose (1) is slipped over the conically slightly thickening outer wall (5) of the rotary sleeve (2), to the point where it is tightly fitted. To this end, the hose coupling (1a) has an internal diameter D6 which is greater than the external diameter D5 of the rotary sleeve (2). The rotary sleeve has, for instance, a conically slightly thickening outer wall (5), so that the external diameter D5 of the rotary sleeve (2) slowly widens up to the end (8) facing the connecting socket.

The rotary sleeve has, for instance, in addition to the conical outer face (5), also a conical inner face (7). This is configured so as to correspond with the socket (6) of the elbow connection (3) and, by virtue of a slight play, enables the smooth turning function of the components. The rotary sleeve (2) has symmetrical extensions (8) of the one-piece (unitary) casing, which can be referred to as lugs. The lugs (8) have an internally arranged undercut (9) or hook portion, which serves for the latching to the socket (6). The socket (6) has for the latching a circumferential bevel or a step (10) on the surface, behind which step the socket tapers slightly, with the external diameter D1. The rotary sleeve (2) has an internal diameter D4 which is smaller than the external diameter D3 of the connecting socket (6).

The lugs (8) reach with the undercut over the step (10) and thus form a snap joint between rotary sleeve (2) and socket (6). The connecting socket (6) has, for instance, a conical surface, which results in the external diameter D3 being smaller than the external diameter D2.

Figure 6:
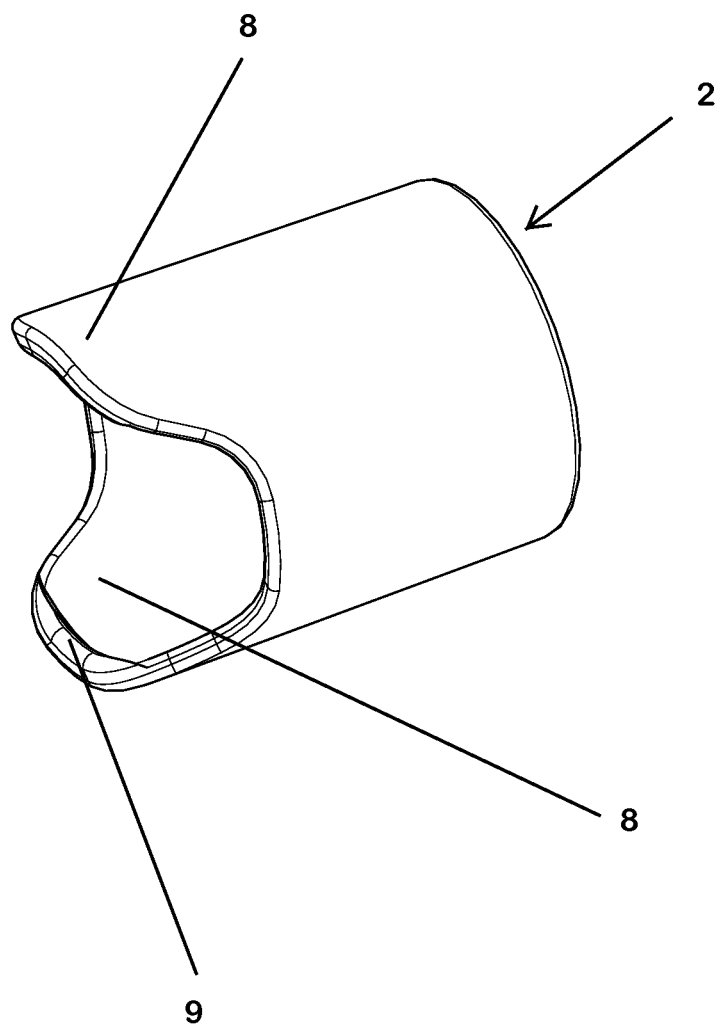
FIG. 6 shows a rotary sleeve.

An axial displacement between the rotary sleeve (2) and the socket is avoided by an end stop (11), against which the socket (6) of the elbow connection (3) can maximally move, in the rotary sleeve (2). The details of the snap joint (undercut 9 and bevel 10), as well as the end stop (11), are evident in the sectional representation. The undercut (9) on the lugs (8) is represented in the detailed view, FIG. 6, of the rotary sleeve (2).

If the connection between hose (t) and mask (4) is to be broken, it is sufficient to pull on the hose coupling (1a) or the hose (1) and the snap joint between socket (6) and rotary sleeve (2) releases. The hose coupling (1a), however, still sits securely on the rotary sleeve (2). If, however, the connection between hose coupling (1a) and rotary sleeve (2) is to be released, for example for cleaning purposes, then the two extended lugs (8) additionally serve as holding or gripping surfaces. For the removal of the hose, the rotary sleeve is grasped via the lugs (8) and so simultaneously secures the snap joint—through the pressure on the lugs—when the hose (1) is pulled off the rotary sleeve (2) by slight bending of the hose coupling (1a).

As a result of the long, smooth overlap region between the rotary sleeve (2) and the socket, substantially fewer leaks occur than with the known, slotted snap joints. To this end, the connecting socket (6) is inserted at least with about 30% of its length, e.g., at least about 40% of its length, at least about 50% of its length, or at least about 60% of its length, into the rotary sleeve (2).

While the present invention has been described with reference to exemplary embodiments, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

REFERENCE NUMERALS 1 respiration hose with
1a hose coupling
2 rotary sleeve
3 elbow connection with ball joint
4 respiration mask (not represented)
5 outer face of the rotary sleeve (2)
6 socket
7 inner face of the rotary sleeve (2)
8 lug
9 undercut
10 bevel, step
11 stop

What is claimed is:

1. A device for connecting a patient interface and a respiration hose, wherein the device comprises a connecting socket configured for being connected to the patient interface and a rotary sleeve configured to be connected to a respiration hose, the connecting socket being insertable at least partially into the rotary sleeve by having an external diameter which is smaller than an internal diameter of the rotary sleeve, the rotary sleeve comprising on its inner side latching elements that engage in latching elements on an external diameter of the connecting socket, and the rotary sleeve being conical so that an external diameter of the rotary sleeve widens up to an end that faces the connecting socket, and the rotary sleeve having symmetrical extensions that are lugs comprised of a one-piece, unitary outer wall.

2. The device of claim 1, wherein the connecting socket is insertable with at least 30% of its length into the rotary sleeve.

3. The device of claim 1, wherein the connecting socket is insertable with at least 60% of its length into the rotary sleeve.

4. The device of claim 1, wherein the connecting socket is insertable with at least 80% of its length into the rotary sleeve.

5. The device of claim 1, wherein the rotary sleeve comprises on its inner wall a stop for the connecting socket.

6. The device of claim 1, wherein the device further comprises a respiration hose coupling having an internal diameter which is greater than an external diameter of the rotary sleeve.

7. The device of claim 1, wherein the rotary sleeve has a conical inner face.

8. The device of claim 1, wherein the lugs comprise on their inner wall an undercut or latching portion which serves for the latching to the connecting socket.

9. The device of claim 1, wherein the external diameter of the connecting socket widens conically in a direction away from the rotary sleeve.

10. The device of claim 1, wherein the connecting socket, for latching to the rotary sleeve, comprises a circumferential bevel or a step in its outer wall.

11. The device of claim 10, wherein the connecting socket tapers behind the step and has an external diameter which is smaller than a conically widened external diameter of the connecting socket.

12. The device of claim 8, wherein the lugs reach with the undercut over a step in the outer wall of the connecting socket to thereby form a snap joint between rotary sleeve and connecting socket.

13. The device of claim 1, wherein an axial displacement between the rotary sleeve and the connecting socket is prevented by an end stop in the rotary sleeve, against which end stop the connecting socket butts.

14. A device for connecting a patient interface and a respiration hose, wherein the device comprises a connecting socket configured for being connected to the patient interface and a rotary sleeve configured to be connected to a respiration hose, the connecting socket being insertable at least partially into the rotary sleeve by having an external diameter which is smaller than an internal diameter of the rotary sleeve, the rotary sleeve having a conical inner face and comprising symmetrical extensions that are lugs comprised of a one-piece, unitary outer wall, which extensions have on its their inner side wall latching elements that engage in latching elements on an external diameter of the connecting socket.

15. The device of claim 14, wherein the device further comprises a respiration hose coupling having an internal diameter which is greater than an external diameter of the rotary sleeve.

16. The device of claim 14, wherein the lugs comprise on their inner wall an undercut or latching portion which serves for the latching to the connecting socket.

17. The device of claim 14, wherein the external diameter of the connecting socket widens conically in a direction away from the rotary sleeve.

18. The device of claim 1, wherein the rotary sleeve has a conically slightly thickening outer wall so that the external diameter of the rotary sleeve widens up to the end that faces the connecting socket.

* * * * *